United States Patent

Pappas et al.

Patent Number: 5,983,711
Date of Patent: Nov. 16, 1999

[54] TEMPERATURE CONTROLLED GRAVIMETRIC MOISTURE ANALYZER AND METHOD THEREFOR

[75] Inventors: William D. Pappas, Tempe; Walfred R. Raisanen, Paradise Valley, both of Ariz.

[73] Assignee: Arizona Instrument Corporation, Phoenix, Ariz.

[21] Appl. No.: 08/999,277

[22] Filed: Dec. 29, 1997

[51] Int. Cl.⁶ .............................. G01N 5/02; G01N 25/00
[52] U.S. Cl. .................................................. 73/76; 374/14
[58] Field of Search ................................. 73/76; 374/14; 702/23; 219/708, 710, 711

[56] References Cited

U.S. PATENT DOCUMENTS

| | | | |
|---|---|---|---|
| Re. 32,861 | 2/1989 | Collins et al. | 73/76 |
| 2,569,749 | 10/1951 | Dietert et al. | 73/76 |
| 3,292,417 | 12/1966 | Hayden et al. | 73/76 |
| 3,902,354 | 9/1975 | Harlan et al. | 73/76 |
| 3,909,598 | 9/1975 | Collins et al. | 235/151.3 |
| 4,165,633 | 8/1979 | Raisanen | 73/76 |
| 4,291,775 | 9/1981 | Collins | 73/76 |
| 4,485,284 | 11/1984 | Pakulis | 374/14 |
| 4,554,132 | 11/1985 | Collins | 422/68 |
| 4,606,650 | 8/1986 | Harris | 374/14 |
| 4,798,252 | 1/1989 | Knothe et al. | 374/14 |
| 4,977,523 | 12/1990 | Mohler et al. | 73/76 |
| 5,499,532 | 3/1996 | Kaiho et al. | 73/76 |

*Primary Examiner*—Benjamin R. Fuller
*Assistant Examiner*—Robin Clark
*Attorney, Agent, or Firm*—Meschkow & Gresham, P.L.C.; Jordan M. Meschkow; Lowell W. Gresham

[57] ABSTRACT

A temperature controlled gravimetric moisture analyzer (20) is used to control the temperature of a sample material (24) while determining moisture content of the sample material (24). The moisture analyzer (20) includes a thermally conductive sample holder (22) having an emissive surface (44). A high precision force balance (30) is coupled to the sample holder (22) for weighing the sample material (24). A heater (26) encloses the sample material. An air temperature sensor (38) is configured to produce an air temperature signal (54). An infrared temperature sensor is configured to detect infrared emissions from the emissive surface (44) to produce a sample temperature signal (60) representative of the temperature of the sample material (24). A controller receives the air and sample temperature signals (54, 60) and controls the heater (26) in response to the signals.

16 Claims, 2 Drawing Sheets

TEMPERATURE CONTROLLED GRAVIMETRIC MOISTURE ANALYZER AND METHOD THEREFOR

TECHNICAL FIELD OF THE INVENTION

The present invention relates generally to an apparatus and a method for measuring change of weight of a material. In particular, the present invention relates to an apparatus and a method for controlling the temperature of a material during thermal gravimetric measurement of moisture content of the material.

BACKGROUND OF THE INVENTION

Determination of moisture (or volatile) content in materials is of such importance in so many fields that a wide variety of devices and analytical methods are used. One method for measuring moisture content in solids and non-volatile liquids is thermal gravimetric. In a thermal gravimetric system, a small sample of material is weighed and then the material is dried by the application of heat thereto and re-weighed after drying. Any difference in weight is indicative of the moisture content.

In one conventional thermal gravimetric moisture analyzer, the sample material is placed on a sample holder which is attached to a high precision scale, and enclosed by an electrically heated chamber. The temperature of the air in the chamber is measured and controlled to a selected value. The selected value is the temperature at which the volatiles in the sample material should be successfully driven off without allowing the sample material to burn. It is assumed that the temperature of the sample material correlates to the air temperature, hence when the air temperature is at the selected value, it is presumed that the sample material is also at the selected value. Following the heating process, the resulting loss of sample weight is automatically determined and displayed.

The electrical heater of the prior art moisture analyzer generates heat energy that has a convective component and a radiative component. The convective component is the heat energy that the sample receives from the movement of the warmed air in the chamber. The radiative component is the heat energy that the sample receives by absorption of infrared radiation emitted from the electrical heater. A problem with this conventional electrical heater is that air does not receive a significant amount of heat energy by absorption of infrared radiation. Thus, the air temperature measurement is primarily a measure of the convective component of the heat energy, not a combined measure of both the convective and radiative components of the heat energy such as that imparted on the sample material. Hence, the air temperature measurement is not an accurate representation of the actual sample temperature.

Furthermore, heating elements of different moisture analyzers have varying levels of radiative emissions. Thus, the radiative component of heat energy may not be consistent between heaters and even from one test time to the next. In addition, radiative absorptivity of the sample material varies from material to material. The radiative absorptivity is the amount of heat that a sample material absorbs from the radiative component of the heat energy generated by the moisture analyzer. Due to these above variations, the sample material temperature cannot be reliably correlated to the measured air temperature.

Unreliable correlation leads to variations in the amount of volatiles lost by the sample material and the rate at which the volatiles are driven off from test to test and from system to system. For example, when the air temperature reaches the selected value, the radiative component of the heat energy may cause the sample temperature to be higher than the air temperature, thus the sample material may undesirably burn and lose hydrocarbons as well as volatiles so that the weight loss is inaccurately high. Whereas, during a different test of the same type of sample material, the radiative component of the heat energy differ from the previous test so that the results from the previous test cannot be correlated with the later test to prevent the excess heating of the sample material and the resulting loss of hydrocarbons.

To circumvent the problems associated with the variability of the radiative component of the heat generated by the electrical heater, other prior art gravimetric moisture analyzer systems utilize a microwave oven to dry a sample material. The microwave heated moisture analyzer solves the problems associated with the electrically heated moisture analyzer because there are no convective and radiative components of heat energy such as that generated by an electrically heated moisture analyzer. As is known in the art, microwave radiation is absorbed by water and polar organic molecules, causing an increase in the molecular motion. Due to the absorption of radiation energy, the water and polar solvents are collectively heated and removed through vaporization and volatilization.

Air temperature inside the microwave oven is not used to control the microwave oven to a preselected value, since microwave heating does not involve the convection of heat energy. Rather, the microwave oven is configured to dry the sample material for a preselected time. The drying time is preselected, based on factors such as the sample size, the magnetron capabilities of the microwave, expected time to achieve volatile loss, and other factors which may be determined by experimentation.

A problem with the microwave heated moisture analyzer is that if the sample is heated for too long of a duration, the microwave radiation may produce hot spots in the sample material which could decompose or destroy part of the sample being tested. Furthermore, since the preselected drying time is determined by experimentation, drying time does not automatically adapt to individual variability of the sample material, such as a higher than normal moisture level in the sample material, unexpected volatile loss, variability of sample size, and so forth. Thus, use of the microwave heated moisture analyzer also introduces inaccuracies into the data.

To gain more accurate and reliable drying of the sample material, it is desirable to directly measure the temperature of the sample material. Unfortunately, in either of the prior art moisture analyzers, it is not possible to directly contact the sample material to obtain a measure of the sample temperature because such direct contact may interfere with the high precision weighing process.

SUMMARY OF THE INVENTION

Accordingly, an advantage of the present invention is that an apparatus and a method are provided that allow accurate control of the dynamics of the heating process in a gravimetric moisture analyzer.

Another advantage of the present invention is that an apparatus and a method are provided that adapt to system and sample material variability in order to reliably and reproducibly drive off volatiles from a sample material.

Another advantage of the present invention is that an apparatus and a method are provided that obtain an accurate representation of the temperature of the sample material during the heating process.

Yet another advantage of the present invention is that an apparatus and method provide a measurement of the sample temperature without interfering with the high precision weighing process in a gravimetric moisture analyzer.

The above and other advantages of the present invention are carried out in one form by a temperature controlled gravimetric moisture analyzer. The analyzer includes a sample holder for retaining a sample material. A weighing mechanism is coupled to the sample holder for weighing the sample material. A heater encloses the sample material, and the heater is configured to heat the sample material. A temperature sensor is located proximate the sample holder and is configured to produce an output signal representative of a temperature of the sample material. A controller receives the output signal and is configured to control the heater in response to the output signal.

The above and other advantages of the present invention are carried out in another form in a temperature controlled gravimetric moisture analyzer by a method of processing a sample material. The method call for retaining the sample material, weighing the sample material, and heating the sample material. The method further calls for measuring a sample temperature of the sample material, controlling a heater element of the moisture analyzer in response to the sample temperature, and weighing the sample material in response to the heating action.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
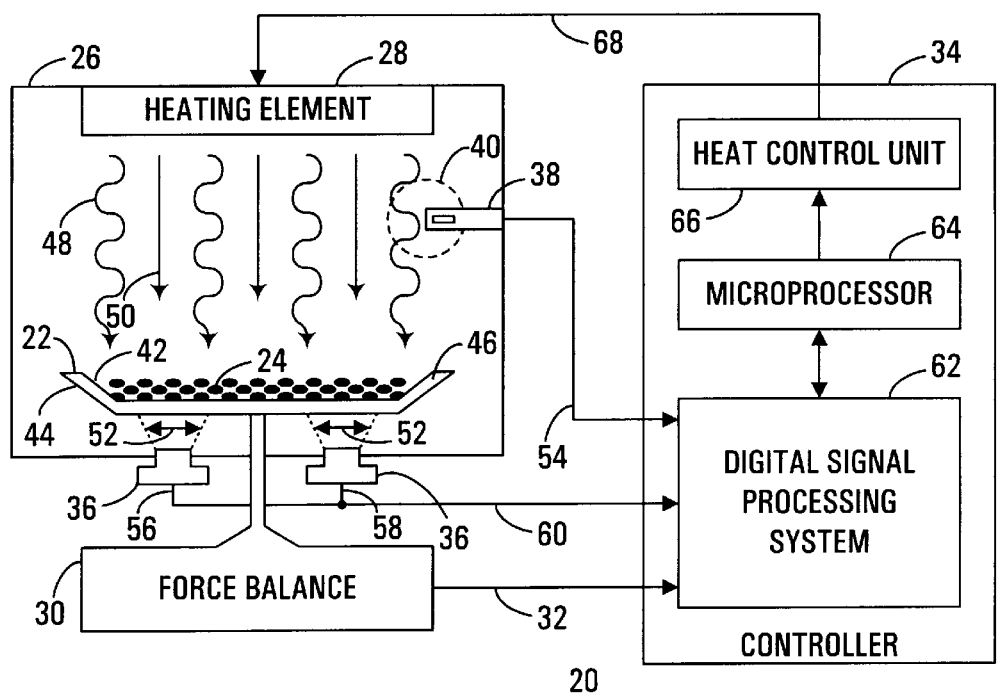
FIG. 1 shows a block diagram of a temperature controlled gravimetric moisture analyzer.

FIG. 1 shows a block diagram of a temperature controlled gravimetric moisture analyzer 20. Moisture analyzer 20 is used to determine moisture content of sample material 24. Moisture analyzer 20 includes a sample holder 22 for retaining a sample material 24. Sample material 24 is a sample of a solid or semi-solid material that is of a porous character for which a measure of the volatile/moisture content is desired.

A heater 26 encloses sample holder 22 and includes a heating element 28 for heating sample material 24. In the preferred embodiment heating element 28 is formed of an alloy of nickel and chromium. Heating element 28 has high electric resistance and the ability to withstand high temperatures for long periods of time. Those skilled in the art will recognize that heating element 28 may be another type of conventional heater such as a vacuum oven, halogen light bulb, microwave oven, and so forth.

A weighing mechanism 30 is positioned in heater 26 and coupled to sample holder 22. Weighing mechanism 30 may be a high precision force balance or any other type of high precision scale known to those skilled in the art. In the preferred embodiment, force balance 30 is a top loading electrobalance which projects through the floor of heater 26. Force balance 30 provides means for obtaining the weight of sample material 24 as sample material 24 is heated in heater 26. Force balance converts the weight to an electrical output signal 32 which is received by a controller 34.

Temperature sensors 36 are also configured to project through the floor of heater 26 proximate sample holder 22. In the preferred embodiment, moisture analyzer 20 includes two temperature sensors 36. Each of temperature sensors 36 is an infrared sensor array configured to detect infrared energy being emitted from sample holder 22. In addition, moisture analyzer 20 includes a temperature sensor 38 positioned in heater 26. Temperature sensor 38 is a resistive temperature device (RTD) for measuring the air temperature at a location 40 proximate heating element 28.

Sample holder 22 has a reflective surface 42 configured to face heating element 28, an emissive surface 44 configured to face infrared sensor arrays 36, and a thermally conductive core 46 located between reflective and emissive surfaces 42 and 44, respectively. Sample holder 22 is desirably a circular flat pan with inclined sides for retaining a thin, uniformly distributed layer of sample material 24. Sample holder 22 is shown in a cross-sectional form in FIG. 1 to illustrate the relationship between reflective surface 42, emissive surface 44, and thermally conductive core 46. Heating element 28 generates heat having a convective component 48, which is the heat energy that sample material 24 absorbs from the movement of warmed air in heater 26. In addition, heating element 28 generates heat having a radiative component 50, which is the heat energy that sample material 24 absorbs from the emission of infrared radiation from heating element 28. Convective and radiative components 48 and 50, respectively, are illustrated in FIG. 1 for clarity of discussion. However, those skilled in the art will recognize that convective and radiative components 48 and 50 are forms of heat energy that are not normally visible.

Sample holder 22 may be formed from a thermally conductive material, such as aluminum. Hence, reflective surface 42 is a shiny aluminum surface which reflects radiative component 50, so that sample holder 22 will not heat up due to absorption of radiative component 50.

Sample material 24 heats in response to radiative component 50 depending upon the infrared absorptivity of sample material 24. Infrared absorptivity is defined herein as the property of sample material 24 that determines the fraction of radiative component 50 absorbable by sample material 24. Differing types of materials will have different infrared absorptivity and will be affected more or less by radiative component 50 depending upon the infrared absorptivity.

Since sample holder 22 includes thermally conductive core 46, as sample material 24 is heated both by convective component 48 and radiative component 50, heat from sample material 24 conducts through conductive core 46 and is emitted from emissive surface 44. Emissivity is defined herein as the ability of a surface to emit radiant energy as compared to the ability of a black body at the same temperature to emit the same level radiant energy. Hence, an emissivity value is a ratio between the emissivity of the surface and a black body. Emissive surface 44 is characterized by an emissivity value of at least 0.9. This emissivity value is realized in the aluminum pan of sample holder 22 by treating the bottom surface of sample holder 22 with a flat black coating, such as paint, in order to produce emissive surface 44.

Due to the characteristics of thermally conductive core 46 and emissive surface 44, the radiant energy detectable by each of infrared sensor arrays 36 represents the heat imparted on sample material 24 by both convective and radiative components 48 and 50, respectively. Therefore, a temperature of sample material 24 can be measured without direct contact of the material so as to not interfere with the high precision measurements of sample weight.

In the preferred embodiment, each of infrared sensor arrays 36 is a thermopile that heats in response to the amount of infrared radiation it senses so as to measure temperature. Each of infrared sensor arrays 36 is configured to have a field-of-view that is no larger than a portion 52 of emissive surface 44. This limited field-of-view prevents infrared sensor arrays 36 from detecting radiative component 50 being emitted from heating element 28, or from detecting any other infrared radiation which may be emitted from the inner surfaces of heater 26.

RTD 38 is configured to produce an electrical output, or air temperature signal 54, which represents heating of air at location 40 by convective component 48. Whereas, infrared sensor arrays 36 are configured to produce first and second electrical outputs 56 and 58, respectively, which represent heating of sample material 24 by both convective and radiative components 48 and 50.

First and second electrical outputs 56 and 58 are combined to form a sample temperature signal 60 that represents the heat imparted on sample material 24. Air temperature signal 54 is and sample temperature signal 60 are received by controller 34. Alternatively, first and second electrical outputs 56 and 58, respectively, may be received by controller 34 to be combined in controller 34.

In the preferred embodiment, two infrared sensor arrays 36 are used to detect infrared radiation being emitted from emissive surface 44. First and second output signals 56 and 58 are then combined by averaging to determine sample temperature signal 60. However, nothing limits the present invention to two infrared sensor arrays. Those skilled in the art will recognize that a single infrared sensor array may be used or more than two sensor arrays may be used depending on the level of temperature sensing accuracy desired and the field-of-view of each of the sensor arrays.

Electrical output signal 32 representing sample weight, air temperature signal 54, and sample temperature signal 60 are received by a digital signal processing system 62 of controller 34. Digital signal processing system 62 filters, amplifies, and converts weight signal 32, air temperature signal 54, and sample temperature signal 60 to digital data. The digital data representing these signals are received by a microprocessor unit 64 where calculations are performed to determine moisture content of sample material 24 and to analyze air temperature signal 54 and sample temperature signal 60. Calculation and analysis routines reside in memory (not shown) of microprocessor 64 and are invoked in response to data received from digital signal processing system 62.

Microprocessor 64 is coupled to a heat control unit 66 which in turn is coupled to heating element 28 via a control line 68. Heat control unit 66 drives heating element 28 in response to one of air temperature and sample temperature signals 54 and 60, respectively.

Figure 2:
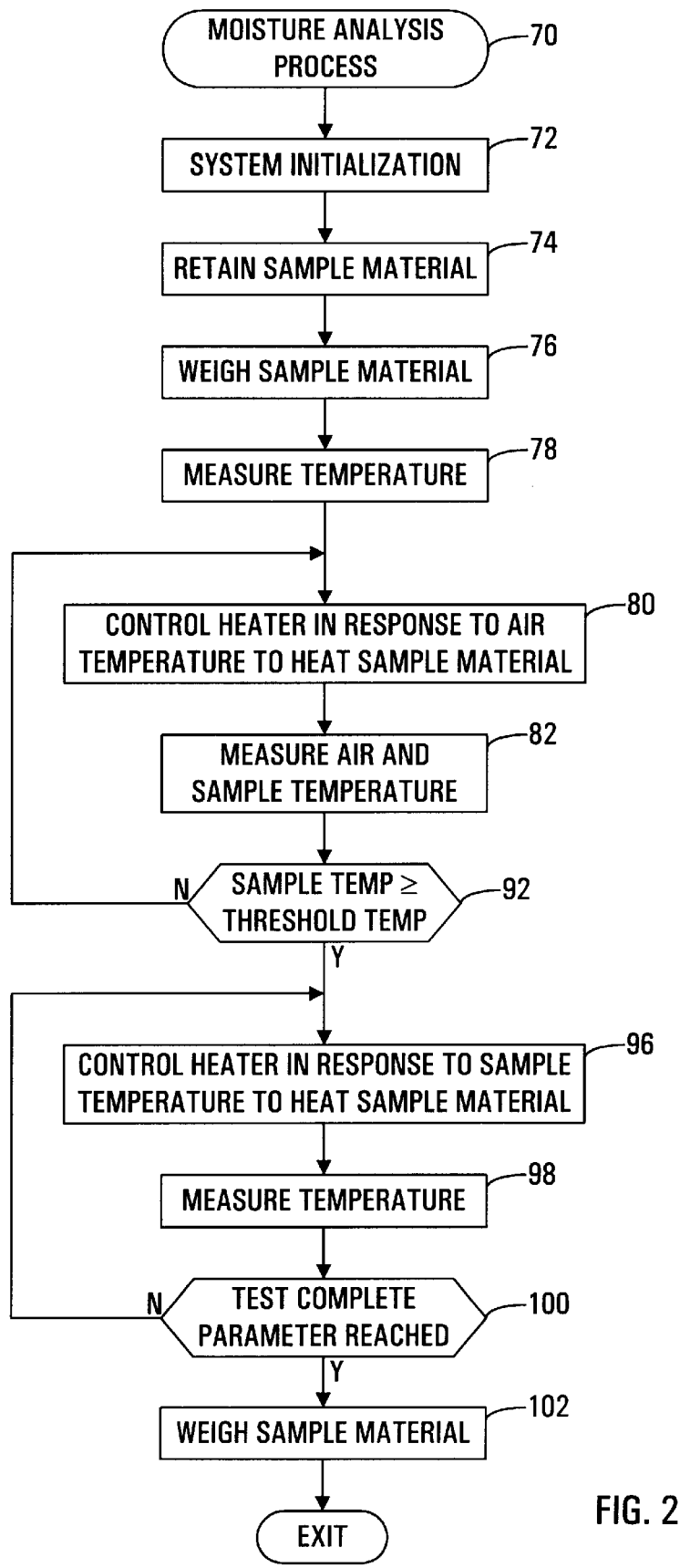
FIG. 2 shows a flow chart of a moisture analyzing process conducted using the temperature controlled gravimetric moisture analyzer.

FIG. 2 shows a flow chart of a moisture analyzing process 70 conducted using the temperature controlled gravimetric moisture analyzer 20 (FIG. 1). Process 70 provides temperature control of heating element 28 (FIG. 1) and measures the volatile/moisture content of sample material 24 (FIG. 1).

Process 70 begins with a task 72. Task 72 causes moisture analyzer 20 (FIG. 1) to begin system initialization. System initialization subtasks include entering data into moisture analyzer 20 such as sample material identification, a desired sample temperature that will successfully and rapidly drive off volatiles, ending criteria for automatically ending a test, and so forth. Ending criteria for indicating when a test is complete can include ending the test when a predicted final value (such as sample temperature) meets certain criteria, when a weight loss rate falls below a selected value, when a selected amount of time has passed, and so forth.

Following initialization task 72, a task 74 is performed. In task 74, sample material 24 (FIG. 1) is retained on sample holder 22 (FIG. 1). Desirably, a thin layer of sample material 24 is uniformly distributed across reflective surface 42 of sample holder 22.

Following task 74, a task 76 is performed. In task 76, sample holder 22 with sample material 24 is placed on force balance 30 (FIG. 1) and enclosed in heater 26. Sample material 24 is then weighed to determine the wet or starting weight. The starting weight of sample material 24 is received as electrical output signal 32 (FIG. 1) by controller 34 (FIG. 1). Those skilled in the art will recognize that weighing task 76 is desirably performed periodically and continuously throughout a test in order to provide a profile of the changing weight of sample material 24 as material 24 is heated.

In conjunction with weighing task 76, other test preparation functions may be occurring, such as obtaining an indication that a door (not shown) of heater 26 (FIG. 1) is closed, nitrogen purge to remove volatiles from heater 26, and so forth that will not be described in detail herein.

Following task 76, a task 78 obtains a measurement of starting temperatures. Controller 34 (FIG. 1) receives air temperature signal 54 (FIG. 1) and sample temperature signal 60 (FIG. 1) in order to obtain a baseline measurement for each of temperature signals 54 and 60.

After task 78, and in response to a begin test signal, a task 80 is performed. Task 80 causes moisture analyzer 20 to begin a moisture analysis test by activating heating element 28. Heat is injected into heater 26 by heating element 28 (FIG. 1) as commanded by microprocessor 64 (FIG. 1) and communicated by heat control unit 66 (FIG. 1) of controller 34 (FIG. 1). Microprocessor 64 controls heating element 28 (FIG. 1) in response to air temperature signal 54. Due to the time lag associated with sample material 24 heating up, conduction of that heat through thermally conductive core 46 (FIG. 1) of sample holder 22 (FIG. 1), and emission of infrared energy from emissive surface 42, heating element 28 is controlled in response to air temperature signal 54. Control in response to air temperature signal 54 produces a rapid rise of temperature to near predetermined temperature 90.

In conjunction with task 80, a task 82 is performed. In task 82, controller 34 (FIG. 1) receives air temperature signal 54 (FIG. 1) and sample temperature signal 60 (FIG. 1). Those skilled in the art will recognize that task 76 is desirably performed periodically and continuously throughout a test in order to provide a profile of the changing temperature of air and sample temperatures as sample material 24 is heated.

Figure 3:
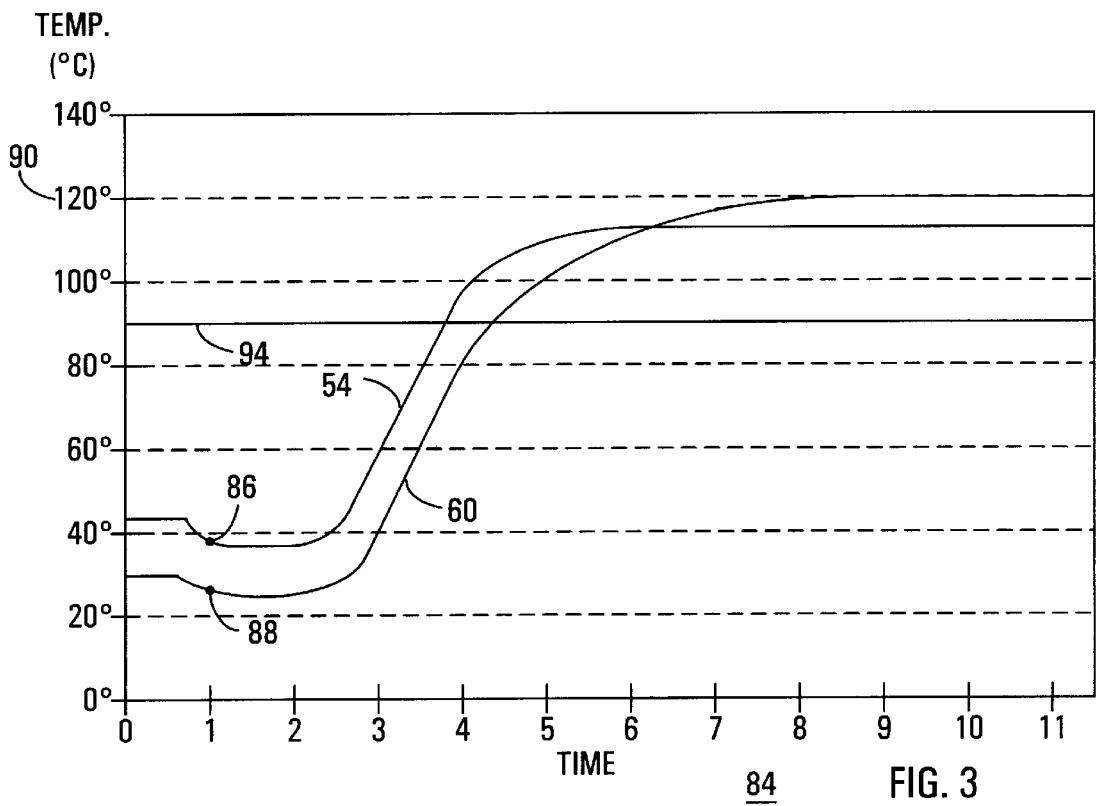
FIG. 3 shows a diagram of an air temperature signal and a sample temperature signal during an exemplary moisture analysis test.

FIG. 3 shows a diagram 84 of air temperature signal 54 and sample temperature signal 60 during an exemplary moisture analysis test. As shown in diagram 84, after an period of sensor stabilization, an initial air temperature measurement 86 and an initial sample temperature measurement 88 are obtained. In the exemplary test shown in diagram 84, a predetermined temperature 90 of one hundred and twenty degrees Celsius has been previously selected. Predetermined temperature 90 is the temperature selected during system initialization in task 72 that is determined to successfully drive off volatiles/moisture from sample material 24.

With reference back to process 70 (FIG. 2), in response to task 82, a query 92 is performed. In query task 92, microprocessor 64 (FIG. 1) of controller 34 (FIG. 1) compares sample temperature signal 60 to a signal representative of a threshold temperature 94 (FIG. 3). Threshold temperature 94 is approximately three quarters of predetermined temperature 90 as illustrated in diagram 84 (FIG. 3). When sample temperature signal 60 is less than threshold temperature 94, process 70 loops back to task 80 and heating element 28 continues to be controlled in response to air temperature signal 54 to heat sample material 24.

When sample temperature signal 60 is greater than or equal to threshold temperature 94, process 70 proceeds with a task 96. In task 96, microprocessor 64 (FIG. 1) sends commands to heat control unit 66 (FIG. 1) to control heating element 28 in response to sample temperature signal 60 and heat sample material 24 (FIG. 1) to predetermined temperature 90.

Microprocessor 64 (FIG. 1) switches to control in response to sample temperature signal 60 when sample temperature signal 60 nears predetermined temperature signal 90 to assure that the temperature of sample material 24, as represented by sample temperature signal 60, is heated to predetermined temperature 90. In other words, control in response to air temperature signal 54 provides coarse temperature control while control in response to sample temperature signal 60 provides fine temperature control to predetermined temperature 90.

In the preferred embodiment, threshold temperature 94 is approximately three quarters of predetermined signal 90. Threshold temperature 94 is selected to provide an optimal point at which sample temperature signal 60 will accurately represent the temperature of the sample. Threshold temperature 94 may be shifted down to at least one half of predetermined signal 90, or may be shifted above three quarters of predetermined signal 90. However, it should be readily apparent to those skilled in the art that if threshold 94 is set too close to predetermined signal 90, the temperature of sample material 24 may overshoot predetermined signal 90 before appropriate control of heating element 28 can be established.

With reference back to process 70, in conjunction with task 96, a task 98 is performed. Task 98 measures sample material temperature. As discussed previously, temperature measurements are desirably obtained frequently in order to form a time versus temperature profile as illustrated in diagram 84 (FIG. 3).

In response to task 98, a query task 100 determines if a test complete parameter has been reached. The test complete parameter was established in task 72 as the ending criteria for which the moisture analysis test is determined to be complete. The ending criteria is specific to sample material 24 (FIG. 1). When a test complete parameter has not been reached, process 70 loops back to task 96 so that controller 34 heats and maintains sample material 24 at predetermined temperature 90.

In query task 100, when the test complete parameter is reached, process 70 proceeds to a task 102 where a final weight of sample material 24 is determined. The final weight is subtracted from the initial weigh determined in task 76 to determine the volatile/moisture content of sample material 24. Following task 102, process 70 is complete.

With reference to diagram 84 (FIG. 3), sample temperature signal 60 becomes greater than air temperature signal 54 as test time increases. As discussed previously, this is caused by the heat imparted on sample material 24 due to radiative component 50 (FIG. 1) produced by heating element 28. Radiative component 50 may vary from test to test and between moisture analyzers. Hence, the difference between air temperature signal 54 and sample temperature signal 60 is variable. Controller 34 (FIG. 1) controls heating element 28 in response to sample temperature signal 60 in order to mitigate the variability of test data caused by radiative component 50 so as to produce more reliable and accurate test results. Moreover, since control of heating element 28 is controlled in response to the temperature of sample material 24, as opposed to air temperature, test results are reproducible despite inherent system variability.

In summary, an apparatus and a method are described that allow accurate control of the dynamics of the heating process in a gravimetric moisturizer by controlling the amount of heat generated in response to the air temperature and the temperature of the sample material. The present invention adapts to system and sample material variability in order to reliably and reproducibly drive off volatiles from the sample material. Furthermore, the present invention obtains accurate representation of the temperature of the sample material during the heating process without interfering with the high precision weighing process.

Although the preferred embodiments of the invention have been illustrated and described in detail, it will be readily apparent to those skilled in the art that various modifications may be made therein without departing from the spirit of the invention or from the scope of the appended claims. For example, the present invention may be adapted for use within a microwave heated moisture analyzer by forming the sample holder out of a material such as glass, and by composing the parts of the force balance projecting into the microwave oven of materials which are transparent to the microwaves to eliminate heating of the balance.

What is claimed is:

1. A temperature controlled gravimetric moisture analyzer, said analyzer comprising:
   a sample holder for retaining a sample material, said sample holder having a reflective surface in contact with said sample material, an emissive surface, and a thermally conductive core located between said reflective and said emissive surfaces;
   a weighing mechanism coupled to said sample holder for weighing said sample material;
   a heater enclosing said sample material and having a heating element configured to face said sample material for heating said sample material;
   a temperature sensor located proximate said emissive surface of said sample holder for detecting radiant energy emitted from said emissive surface as said sample material is being heated, said temperature sensor producing an output signal representative of a temperature of said sample material; and
   a controller for receiving said output signal and configured to control said heater in response to said output signal.

2. An analyzer as claimed in claim 1 wherein said temperature sensor is a first temperature sensor, said output signal is a first output signal, and said analyzer further comprises a second temperature sensor positioned proximate said heating element of said heater and configured to produce a second output signal representative of a temperature at a location proximate said heating element as said sample material is being heated.

3. An analyzer as claimed in claim 2 wherein said controller is configured to receive said second output signal and said controller is further configured to control said heating element in response to said second output signal.

4. An analyzer as claimed in claim 2 wherein said second temperature sensor is a resistive temperature device for measuring the air temperature at said location.

5. An analyzer as claimed in claim 1 wherein said emissive surface is characterized by an emissivity value, said emissivity value being at least 0.9.

6. An analyzer as claimed in claim 1 wherein said temperature sensor is an infrared detector configured to detect infrared energy being emitted from a portion of said emissive surface.

7. An analyzer as claimed in claim 1 wherein:
said heating element generates heat having a convective component and a radiative component;
said temperature of said sample material is affected by both of said convective and radiative components; and
said output signal represents heat imparted on said sample material by both of said convective and radiative components.

8. An analyzer as claimed in claim 1 wherein:
said heating element is configured to heat said sample material to a predetermined temperature exhibiting a predetermined signal; and
said controller is configured to control said heating element in response to said output signal when said output signal is at least half of said predetermined signal.

9. An analyzer as claimed in claim 1 wherein:
said heating element is configured to heat said sample material to a predetermined temperature; and
said controller is configured to control said heating element to maintain said sample material at said predetermined temperature until a test complete parameter is reached.

10. An analyzer as claimed in claim 6 wherein said sample holder is positioned between said infrared detector and said heater.

11. In a temperature controlled gravimetric moisture analyzer which includes a thermally conductive sample holder having an emissive surface, a heater, and an infrared temperature sensor, a method of processing a sample material, said method comprising the steps of:
(a) distributing said sample material in said thermally conductive sample holder;
(b) enclosing said sample material in said heater;
(c) weighing said sample material;
(d) positioning said infrared temperature sensor proximate said emissive surface;
(e) heating said sample material;
(f) detecting infrared energy emitted from said emissive surface in response to said step (e) to measure a sample temperature of said sample material;
(g) controlling said heating element in response to said sample temperature; and
(h) weighing said sample material in response to said step (e).

12. A method as claimed in claim 11 wherein said heating step heats said sample material to a predetermined temperature, and said method further comprises the steps of:
measuring an air temperature proximate said heating element prior to said step (g);
controlling said heating element in response to said air temperature prior to said step (g); and
performing said step (g) when said sample temperature is at least half of said predetermined temperature.

13. A temperature controlled gravimetric moisture analyzer comprising:
a thermally conductive sample holder having a reflective surface and an emissive surface, said reflective surface being in contact with a sample material;
a weighing mechanism coupled to said sample holder for weighing said sample material;
a heater enclosing said sample material and having a heating element configured to face said reflective surface for heating said sample material;
an air temperature sensor positioned at a location proximate said heating element for producing an air temperature signal representative of an air temperature at said location as said sample material is being heated;
a sample temperature sensor positioned proximate said emissive surface of said sample holder for detecting radiant energy emitted from said emissive surface as said sample material is being heated, and configured to produce a sample temperature signal representative of a sample temperature of said sample material; and
a controller for receiving said air and sample temperature signals and configured to control said heating element in response to said air and sample temperature signals.

14. An analyzer as claimed in claim 13 wherein:
said heating element is configured to heat said sample material to a predetermined temperature;
said controller is configured to control said heating element in response to said air temperature signal when said sample temperature is less than at least half of said predetermined temperature; and
said controller is further configured to control said heating element in response to said sample temperature signal when said sample temperature is at least half of said predetermined temperature.

15. An analyzer as claimed in claim 13 wherein:
said heating element generates heat having a convective component and a radiative component;
said air temperature is affected by said convective component;
said sample temperature is affected by both of said convective and radiative components;
said air temperature signal represents heating of air at said location by said convective component; and
said sample temperature signal represents heat imparted on said sample material by both of said convective and radiative components.

16. An analyzer as claimed in claim 13 wherein said sample temperature sensor is an infrared sensor array configured to detect infrared energy being emitted from said emissive surface.

* * * * *